(12) United States Patent
Xu et al.

(10) Patent No.: US 11,007,362 B1
(45) Date of Patent: May 18, 2021

(54) SYSTEMS AND METHODS FOR INSERTING A PERI-STRAIGHT ELECTRODE ARRAY INTO A COCHLEA OF A RECIPIENT

(71) Applicant: Advanced Bionics AG, Staefa (CH)

(72) Inventors: Bing Xu, Valencia, CA (US); Mark B. Downing, Valencia, CA (US); Leonid M. Litvak, Los Angeles, CA (US)

(73) Assignee: Advanced Biomes AG, Staefa (CH)

( * ) Notice: Subject to any disclaimer, the term of this patent is extended or adjusted under 35 U.S.C. 154(b) by 258 days.

(21) Appl. No.: 16/194,268

(22) Filed: Nov. 16, 2018

(51) Int. Cl.
*A61N 1/05* (2006.01)
*A61F 11/00* (2006.01)

(52) U.S. Cl.
CPC .......... *A61N 1/0541* (2013.01); *A61F 11/004* (2013.01)

(58) Field of Classification Search
CPC ............ A61N 1/36038; A61N 1/36039; A61N 1/0541; A61M 25/0138; A61F 11/004; A61F 11/04; A61F 11/045; A61F 11/00
See application file for complete search history.

(56) References Cited

U.S. PATENT DOCUMENTS

| | | | |
|---|---|---|---|
| 6,421,569 B1 | 7/2002 | Treaba et al. | |
| 7,184,843 B1 | 2/2007 | Cohen | |
| 7,792,586 B2 * | 9/2010 | Dadd | A61B 17/3468 607/57 |
| 8,311,649 B2 | 11/2012 | Frijns et al. | |
| 8,805,546 B2 | 8/2014 | Dadd et al. | |
| 8,909,349 B2 * | 12/2014 | Dadd | A61F 11/00 607/57 |
| 9,381,040 B2 | 7/2016 | Jolly et al. | |
| 9,415,208 B2 * | 8/2016 | Dadd | A61B 17/3468 |
| 9,480,838 B2 | 11/2016 | Jolly et al. | |
| 10,543,125 B2 * | 1/2020 | Dadd | A61N 1/0541 |
| 2002/0029074 A1 * | 3/2002 | Treaba | A61N 1/0541 607/137 |
| 2006/0241723 A1 * | 10/2006 | Dadd | A61B 17/3468 607/57 |
| 2009/0030483 A1 * | 1/2009 | Risi | A61N 1/36038 607/57 |

(Continued)

FOREIGN PATENT DOCUMENTS

| | | |
|---|---|---|
| EP | 3024537 | 10/2018 |
| WO | 2018/080955 | 5/2018 |

*Primary Examiner* — Katrina M Stransky
(74) *Attorney, Agent, or Firm* — ALG Intellectual Property, LLC

(57) ABSTRACT

An exemplary method of inserting a peri-straight electrode array into a cochlea of a recipient includes positioning the peri-straight electrode array and an insertion tool within the recipient such that a distal end of the insertion tool is provided within the recipient at a location that is outside and not touching the cochlea of the recipient, and a straight distal portion of the peri-straight electrode array extends away from the distal end of the insertion tool and into the cochlea. The exemplary method further includes manually interacting with the insertion tool to advance the straight distal portion and at least some of a pre-curved proximal portion into the cochlea without allowing the insertion tool to enter or come in contact with the cochlea, and removing the insertion tool from the recipient such that the peri-straight electrode array remains within the cochlea after the insertion tool is removed from the recipient.

20 Claims, 14 Drawing Sheets

(56) References Cited

U.S. PATENT DOCUMENTS

| | | | | |
|---|---|---|---|---|
| 2011/0022145 A1* | 1/2011 | Beerling | ............... | A61N 1/0541 |
| | | | | 607/137 |
| 2011/0218548 A1* | 9/2011 | Dadd | .................... | A61N 1/0541 |
| | | | | 606/129 |
| 2015/0258331 A1* | 9/2015 | Dadd | ................. | A61B 17/3468 |
| | | | | 606/129 |
| 2016/0361202 A1* | 12/2016 | Dadd | ....................... | A61F 11/00 |
| 2017/0367733 A1 | 12/2017 | Murphy et al. | | |

* cited by examiner

SYSTEMS AND METHODS FOR INSERTING A PERI-STRAIGHT ELECTRODE ARRAY INTO A COCHLEA OF A RECIPIENT

BACKGROUND INFORMATION

Cochlear implant systems are used to provide, restore, and/or improve the sense of hearing to recipients with severe or profound hearing loss. A key component of a cochlear implant system is an electrode lead that is inserted into a cochlea of the recipient in a delicate surgical procedure referred to herein as an "insertion procedure." Insertion procedures are difficult due to the structure of the human cochlea, which is in the shape of a spiral beginning at a base and ending at an apex.

Current cochlear electrode lead technologies include designs in which at least a portion of cochlear electrode lead is pre-curved. Such pre-curved cochlear electrode leads are manufactured in an already-curled shape and are straightened before implantation using either a stylet that is inserted into a lumen of the pre-curved cochlear electrode lead or by using a straight rigid sheath provided around the pre-curved cochlear electrode lead. While a surgeon inserts a pre-curved cochlear electrode lead into the cochlea, the stylet or sheath is gradually withdrawn, which allows the pre-curved cochlear electrode lead to return to its curled shape and conform with the helical shape of the cochlea.

Typically, specialized surgical tools and surgical techniques are required to handle the pre-curved cochlear electrode lead and remove the stylet or sheath. Such techniques can be challenging and require specialized training and experience to perform correctly. Improper insertion of a pre-curved cochlear electrode lead can result in damage to the electrode lead, damage to the cochlear tissue, and/or improper electrode placement in the cochlea (e.g., translocation, tip foldover, etc.). Moreover, typical insertion procedures that utilize specialized surgical tools such as the stylet or sheath include having at least a portion of the stylet or sheath abut against and/or enter into the insertion opening (cochleostomy/round window) of the cochlea during the insertion procedure. This results in loss of visibility and/or tactile feedback for the surgeon and/or increases the chance for intra-cochlear trauma.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
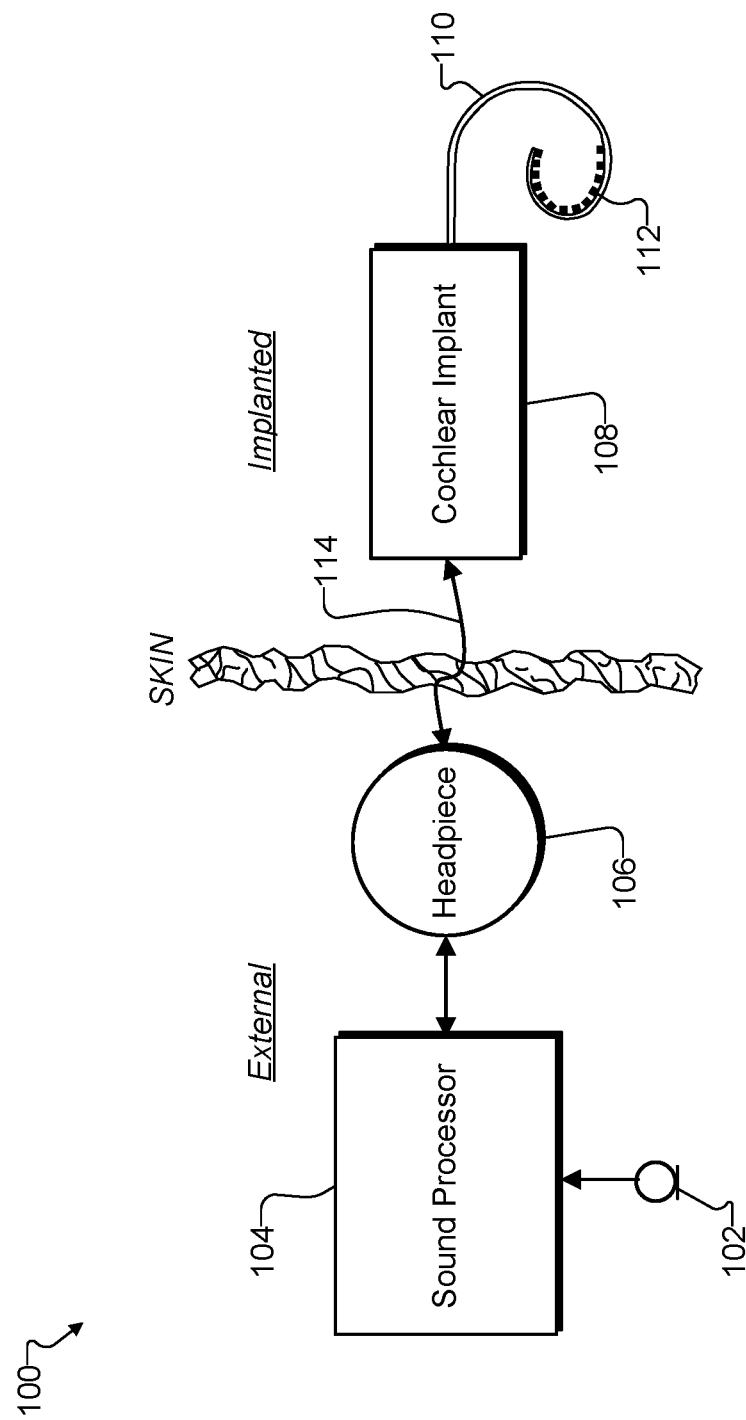
FIG. 1 illustrates an exemplary cochlear implant system according to principles described herein.

Systems and methods for inserting a peri-straight electrode array into a cochlea of a recipient are described herein. As will be described in more detail below, an exemplary method of inserting a peri-straight electrode array into a cochlea of a recipient comprises positioning the peri-straight electrode array and an insertion tool (e.g., a tube or a stylet) within the recipient such that a distal end of the insertion tool is provided within the recipient at a location that is outside and not touching the cochlea (e.g., outside and not touching the cochleostomy or the round window) of the recipient, and a straight distal portion of the peri-straight electrode array extends away from the distal end of the insertion tool and into the cochlea. The method further includes manually interacting with the insertion tool to advance the straight distal portion and at least some of a pre-curved proximal portion of the peri-straight electrode array into the cochlea without allowing the insertion tool to enter or come in contact with the cochlea, and removing the insertion tool from the recipient such that the peri-straight electrode array remains within the cochlea after the insertion tool is removed from the recipient.

As will be described in more detail below, an exemplary system includes a peri-straight electrode array configured to be inserted within a cochlea of a recipient and an insertion tool onto which the peri-straight electrode array is configured to be loaded. The insertion tool is loaded onto the peri-straight electrode array such that a straight distal portion of the peri-straight electrode array extends beyond a distal end of the insertion tool. The peri-straight electrode array and the insertion tool are positioned with respect to each other prior to insertion such that 40% to 60% of the peri-straight electrode array extends distally beyond the distal end of the insertion tool. Such a configuration facilitates positioning the peri-straight electrode array within the cochlea of the recipient without the insertion tool entering into or coming in contact with the cochlea during insertion of the peri-straight electrode array into the cochlea.

The methods and systems for inserting a peri-straight electrode array described herein may provide various benefits to cochlear implant recipients, as well as to surgeons and others involved with insertion procedures. For example, because the insertion tool does not enter or come in contact with the cochlea, it is less likely that the insertion procedure will cause damage to the round window or the cochleostomy of the cochlea of the recipient. In addition, because the insertion tool is provided within the recipient at a location that is outside and not touching the cochlea during the insertion procedure, the surgeon may not lose visibility or tactile feedback, which may assist in correctly positioning the peri-straight electrode array within the cochlea. Moreover, the relative amount that the straight distal portion of the peri-straight electrode array extends beyond the distal end of the insertion tool results in a more flexible cochlear electrode lead that is able to achieve deeper insertion within the cochlea with less trauma than conventional cochlear electrode leads. Accordingly, methods and systems for inserting peri-straight electrode arrays such as those described herein are easier to perform and result in less intra-cochlea trauma than conventional insertion procedures.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. Although FIG. 1 shows a distal end of electrode lead 110 as being curved, it is understood that, according to the examples described below, electrode lead 110 includes a pre-curved proximal portion and a straight distal portion provided at the distal end. It will be understood that one or more other electrodes (e.g., including a ground electrode, not explicitly shown in FIG. 1) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. Various embodiments of electrode lead 110 will be described herein. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a device like the Clinical Programming Interface ("CPI") device from Advanced Bionics, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
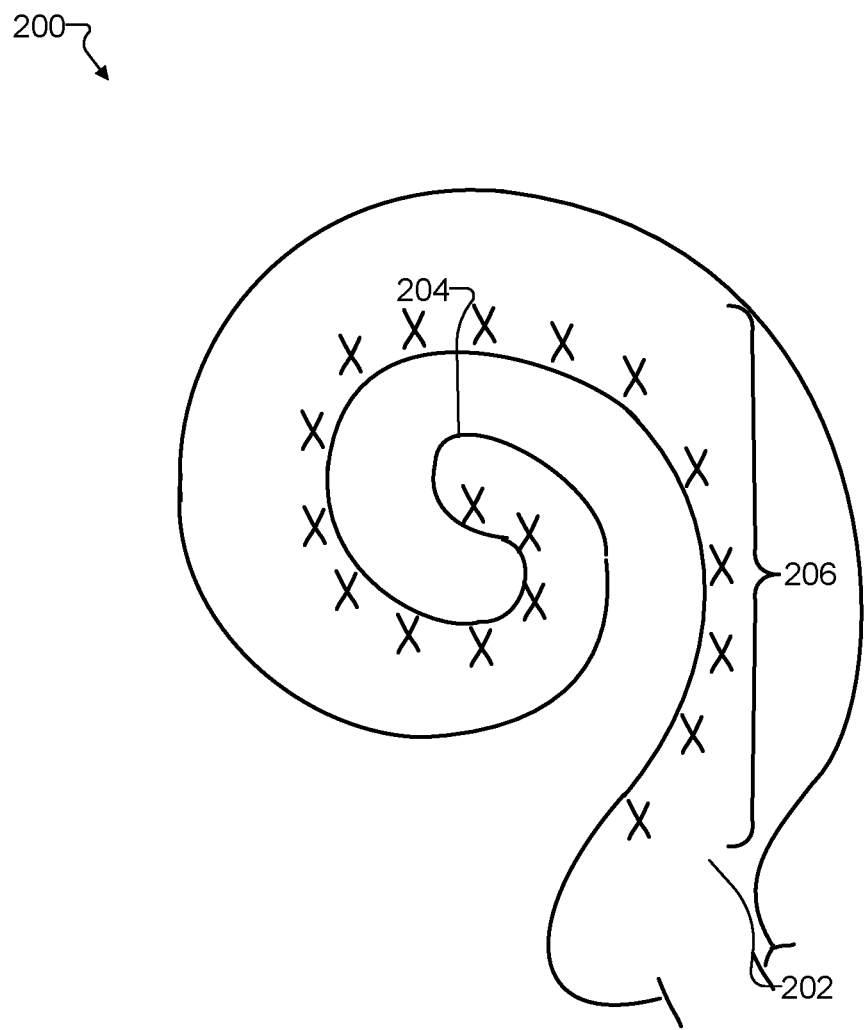
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

As described in more detail below, the methods and systems are directed to insertion of a peri-straight electrode array into the cochlea of the recipient. As used herein, a "peri-straight electrode array" refers to an electrode array that includes electrodes 112 arranged along a straight distal portion and a pre-curved proximal portion. The peri-straight electrode array may generally be referred to as a region of electrode lead 110 that that extends from a distalmost tip of electrode lead 110 to a proximal side of a most proximal electrode included in electrodes 112.

The straight distal portion of the peri-straight electrode array has a native straight state but is sufficiently flexible to conform to and follow a trajectory of the scala tympani of the cochlea during insertion. Examples of straight distal portions of a peri-straight electrode array are provided herein.

The pre-curved proximal portion of the peri-straight electrode array has a native curved state but is sufficiently flexible so as to straighten when loaded onto an insertion tool prior to insertion. After and/or during insertion, the pre-curved proximal portion returns to its native curved state so as to conform to the helical shape of cochlea 200. In certain examples, the pre-curved proximal portion of the peri-straight electrode array may include an additional element (e.g., a shape memory polymer element, a nitinol element, etc.) that causes the pre-curved proximal portion to have the native curved state. Examples of pre-curved proximal portions of a peri-straight electrode array are provided herein.

Peri-straight electrode arrays such as those described herein may be formed of any suitable material as may serve a particular implementation. For example, a peri-straight electrode array may be formed of silicone or any other suitable biocompatible material or combination of biocompatible materials. Various exemplary peri-straight electrode arrays will now be described with reference to FIGS. 3-12.

Figure 3:
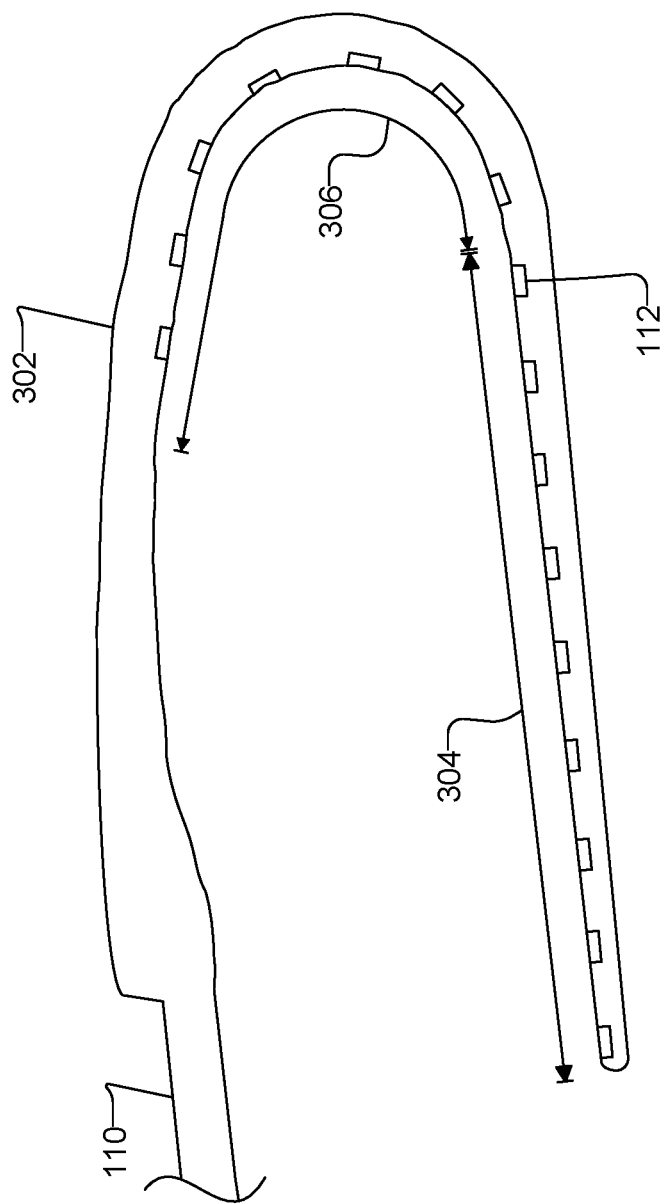
FIG. 3 illustrates a side view an exemplary electrode lead that includes a peri-straight electrode array according to principles described herein.

FIG. 3 illustrates an exemplary electrode lead 110 that includes a peri-straight electrode array 302 having a straight distal portion 304 and a pre-curved proximal portion 306. As shown in FIG. 3, peri-straight electrode array 302 includes a plurality of electrodes 112 that are spaced apart along a side of electrode lead 110. Any suitable number of electrodes 112 may be provided along electrode lead 110 as may serve a particular implementation. In the example shown in FIG. 3, sixteen total electrodes 112 are illustrated. At least some of electrodes 112 are provided along straight distal portion 304 whereas other electrodes 112 are provided along pre-curved proximal portion 306. Straight distal portion 304 may extend along any suitable length of peri-straight electrode array 302 as may serve a particular implementation. In the example shown in FIG. 3, straight distal portion 304 extends along a length of peri-straight electrode array 302 that includes nine of electrodes 112 and pre-curved proximal portion 306 extends along a length of peri-straight electrode array 302 that includes seven of electrodes 112.

As shown in FIG. 3, straight distal portion 304 is in its native straight state and pre-curved proximal portion 306 is in its native curved state, which has a radius of curvature that is configured to conform to the helical shape of the cochlea. Pre-curved proximal portion 306 corresponds to a region of peri-straight electrode array 302 that is configured to achieve a peri-modiolar placement in the cochlear mid basal turn. Because pre-curved proximal portion 306 has a native curved state, pre-curved proximal portion 306 needs to be straightened prior to insertion within cochlea 200. This may be accomplished in any suitable manner. As will be described in more detail below, pre-curved proximal portion 306 may be straightened through the use of an insertion tool such as a stylet or a tube prior to beginning the insertion procedure.

The combination of peri-straight electrode array 302 with an insertion tool may be referred to herein as an assembly or a system that is used during an insertion procedure to position peri-straight electrode array 302 within the cochlea. In certain examples, such assemblies or systems may be provided by a manufacturer as a kit in which the insertion tool is pre-loaded onto peri-straight electrode array 302. Alternatively, an insertion tool may be initially provided separately from peri-straight electrode array 302 and have to be assembled after receipt from the manufacturer. Prior to beginning the insertion procedure, a surgeon or others involved with insertion procedures may load or re-load the insertion tool onto peri-straight electrode array 302 in any suitable manner such that straight distal portion 304 extends away from the insertion tool prior to being inserted into the recipient. In certain examples, an additional separate insertion tool may be used to facilitate re-loading the insertion tool onto peri-straight electrode array 302.

An insertion tool may be loaded onto peri-straight electrode array 302 in any suitable manner. As used herein, the expression "loaded onto" is intended to cover implementations where the insertion tool is inserted within peri-straight electrode array 302 as well as implementations where the insertion tool is provided outside of (e.g., covers at least a part of) peri-straight electrode array 302. For example, a stylet may be provided within a lumen included in electrode lead 110 so as to straighten per-curved proximal portion 306. Examples of electrode arrays that are straightened with a stylet are found in U.S. Pat. No. 8,311,649, which is hereby incorporated by reference in its entirety. Alternatively, a tube may be provided around a portion of the peri-straight electrode array 302 so as to straighten pre-curved proximal portion 306.

Regardless of which type of insertion tool is used, assemblies such as those described herein include positioning the insertion tool with respect to peri-straight electrode array 302 such that at least a certain length of straight distal portion 304 extends beyond a distal end of the insertion tool. In certain examples, the length that straight distal portion 304 extends beyond the distal end of the insertion tool is long enough for straight distal portion 304 to make the first turn in the cochlea prior to pre-curved proximal portion 306 entering cochlea 200 and without the insertion tool entering or coming into contact with cochlea 200. For example, at least 8 mm of straight distal portion 304 may extend distally beyond the distal end of the insertion tool prior to the assembly being inserted into the recipient. It follows therefor that, in such examples, at least 8 mm of straight distal portion 304 enters cochlea 200 prior to pre-curved proximal portion 306 entering cochlea 200.

In certain examples, 40% to 60% of peri-straight electrode array 302 may extend distally beyond a distal end of the insertion tool prior to the assembly being inserted into the recipient. This in turn means that, in such examples, the insertion tool is loaded onto 40% to 60% of peri-straight electrode array 302. To illustrate an example, peri-straight electrode array 302 may be a relatively short electrode array that is 18 mm long with straight distal portion that is 10 mm long and pre-curved proximal portion that is 8 mm long. In such an example, a higher percentage of peri-straight electrode array 302 may extend beyond the distal end of the insertion tool to ensure there is a distally extending portion of at least 8 mm. For example, the percentage may be 50%, which would mean that, in such an example, 9 mm of peri-straight electrode array 302 would extend distally beyond a distal end of the insertion tool. In another example in which a relatively longer peri-straight electrode array 302 is used, a smaller percentage of peri-straight electrode array 302 may extend distally beyond the distal end of the insertion tool. To illustrate an example, peri-straight electrode array 302 may be 24 mm long with straight distal portion 302 that is 12 mm long and pre-curved proximal portion 306 that is 12 mm long. In such an example, a relatively lower percentage of peri-straight electrode array 302 may extend beyond the distal end of the insertion tool to ensure there is a distally extending portion of at least 8 mm. In such an example, the percentage may be 40%, which would mean that 9.6 mm of peri-straight electrode array 302 would extend distally beyond a distal end of the insertion tool.

Figure 4:
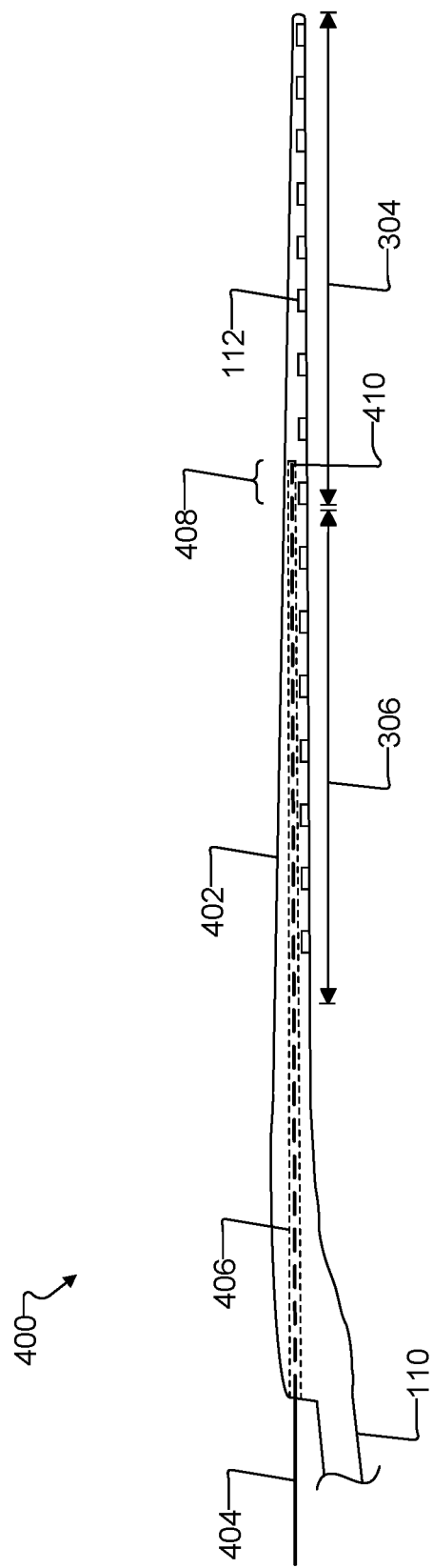
FIG. 4 illustrates a side view of an exemplary assembly including a peri-straight electrode array that has been straightened using a stylet according to principles described herein.

FIG. 4 illustrates a side view of an exemplary assembly 400 in which a peri-straight electrode array 402 is straightened by way of a stylet 404 provided within a lumen 406 of electrode lead 110. In the example shown in FIG. 4, lumen 406 and certain portions of stylet 404 are illustrated in broken lines because they are embedded within electrode lead 110. Stylet 404 may be formed of any suitable material so long as stylet 404 is sufficiently rigid to straighten pre-curved proximal portion 306 when stylet 404 is inserted into a lumen 406. For example, stylet 404 may be made of a platinum-iridium alloy (e.g., Pt/Ir 90/10, 80/20, etc.) or any other suitable material or combination of materials. In certain examples, stylet 404 may be formed of a relatively more deformable material than conventional stylets to reduce contact forces and potential trauma that may occur with a relatively stiffer stylet.

Additionally or alternatively, a distal end of stylet 404 may be relatively smaller than other portions of stylet 404 to further reduce the possibility of intra-cochlear trauma. For example, a proximal end of stylet 404 may have a first diameter and the distal end of stylet 404 may have a second diameter that is smaller than the first diameter. With such a configuration it is possible to further reduce the possibility of intra-cochlear trauma should the distal end of stylet 404 inadvertently enter cochlea 200.

As shown in FIG. 4, a distal portion 408 of lumen 406 overlaps straight distal portion 304. As such, when stylet 404 is fully inserted within lumen 406 a distal end 410 of stylet 404 also overlaps straight distal portion 304. With such a configuration, it is possible to keep the straight distal portion 304 substantially straight with respect to the straightened pre-curved proximal portion 306 when stylet 404 is inserted in lumen 406. Distal portion 408 may overlap straight distal portion 304 by any suitable amount. For example, distal portion 408 may overlap distal straight portion 304 by approximately 1 mm to 4.5 mm.

Figure 5:
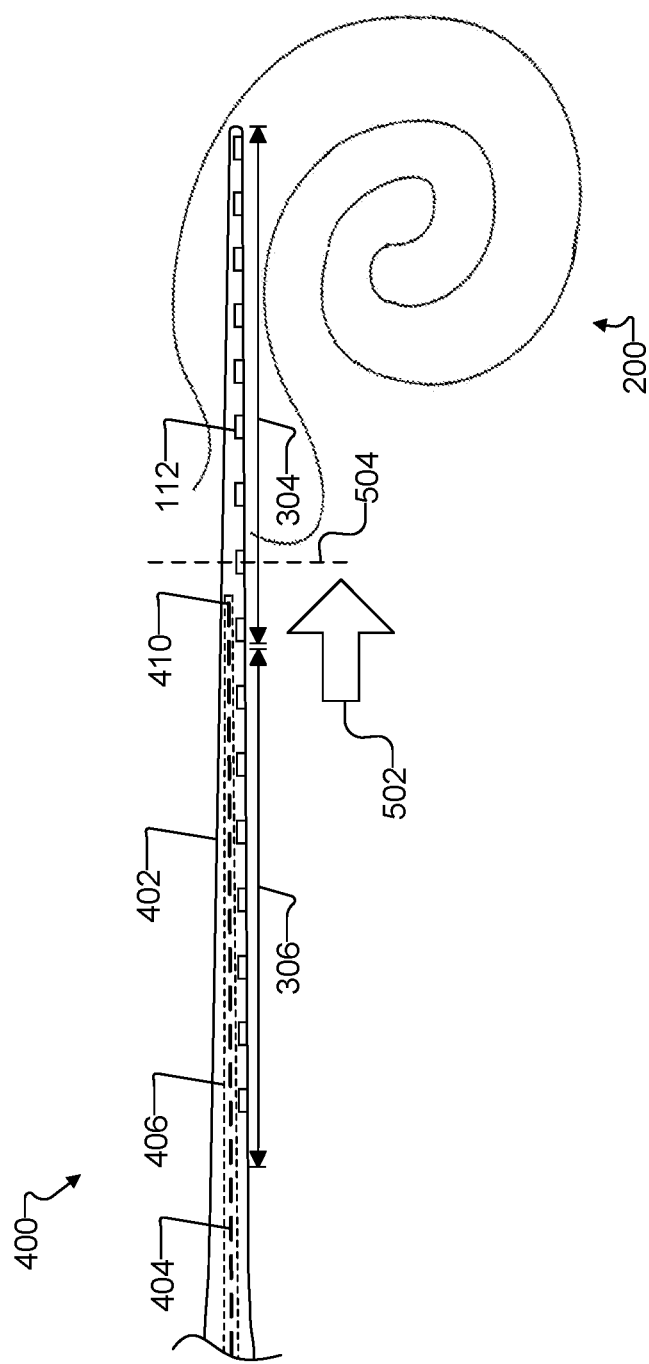
FIGS. 5 and 6 illustrate positions of a peri-straight electrode array during an exemplary insertion procedure that utilizes the assembly illustrated in FIG. 4 according to principles described herein.

FIG. 5 shows a position of a peri-straight electrode array during an exemplary insertion procedure in which assembly 400 shown in FIG. 4 is used. As shown in FIG. 5, assembly 400 is advanced in any suitable manner in the direction of arrow 502 into cochlea 200 such that straight distal portion 304 extends into cochlea 200. Assembly 400 is advanced such that distal end 410 of stylet 404 does not exceed a position indicated by dashed line 504, which is outside of cochlea 200. The position indicated by dashed line 504 may be any suitable distance away from cochlea 200. For example, the position indicated by dashed line 504 may be 1 mm or more away from cochlea 200.

Figure 6:
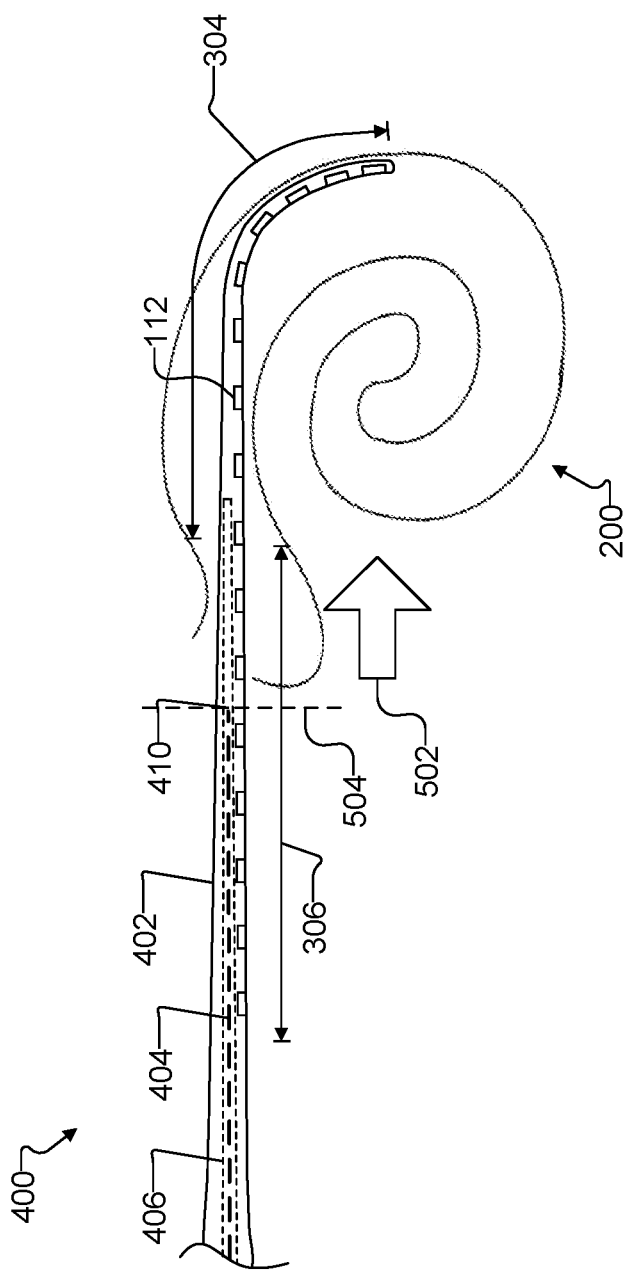

Once stylet 404 reaches the position indicated by dashed line 504 in FIG. 5, electrode lead 110 is advanced off of stylet 404 and further into cochlea 200. This may be accomplished in any suitable manner. For example, electrode lead 110 may be pushed in the direction of arrow 502 by another tool (e.g., a pusher rod) while stylet 404 remains at a position that is to the left of dashed line 504. To illustrate, FIG. 6 shows peri-straight electrode array 402 being advanced off of stylet 404 while stylet 404 remains outside of cochlea 200. The entire insertion procedure is performed without stylet 404 entering into or contacting cochlea 200 any point during the insertion procedure. As straight distal portion 304 of peri-straight electrode array 402 enters further within cochlea 200, straight distal portion 304 flexes so as to generally follow a trajectory of a lateral wall of the cochlea. Straight distal portion follows the lateral wall to achieve a lateral position near apex 204 of cochlea 200. As pre-curved proximal portion 306 is advanced off of stylet 404, pre-curved proximal portion 306 returns to its native curved state so as to conform with the helical shape of cochlea 200 and achieve a peri-modiolar placement in the cochlear mid basal turn.

Once peri-straight electrode array 402 is positioned within cochlea 200, stylet 404 is removed from the recipient such that peri-straight electrode array 402 remains within cochlea 200.

Figure 7:
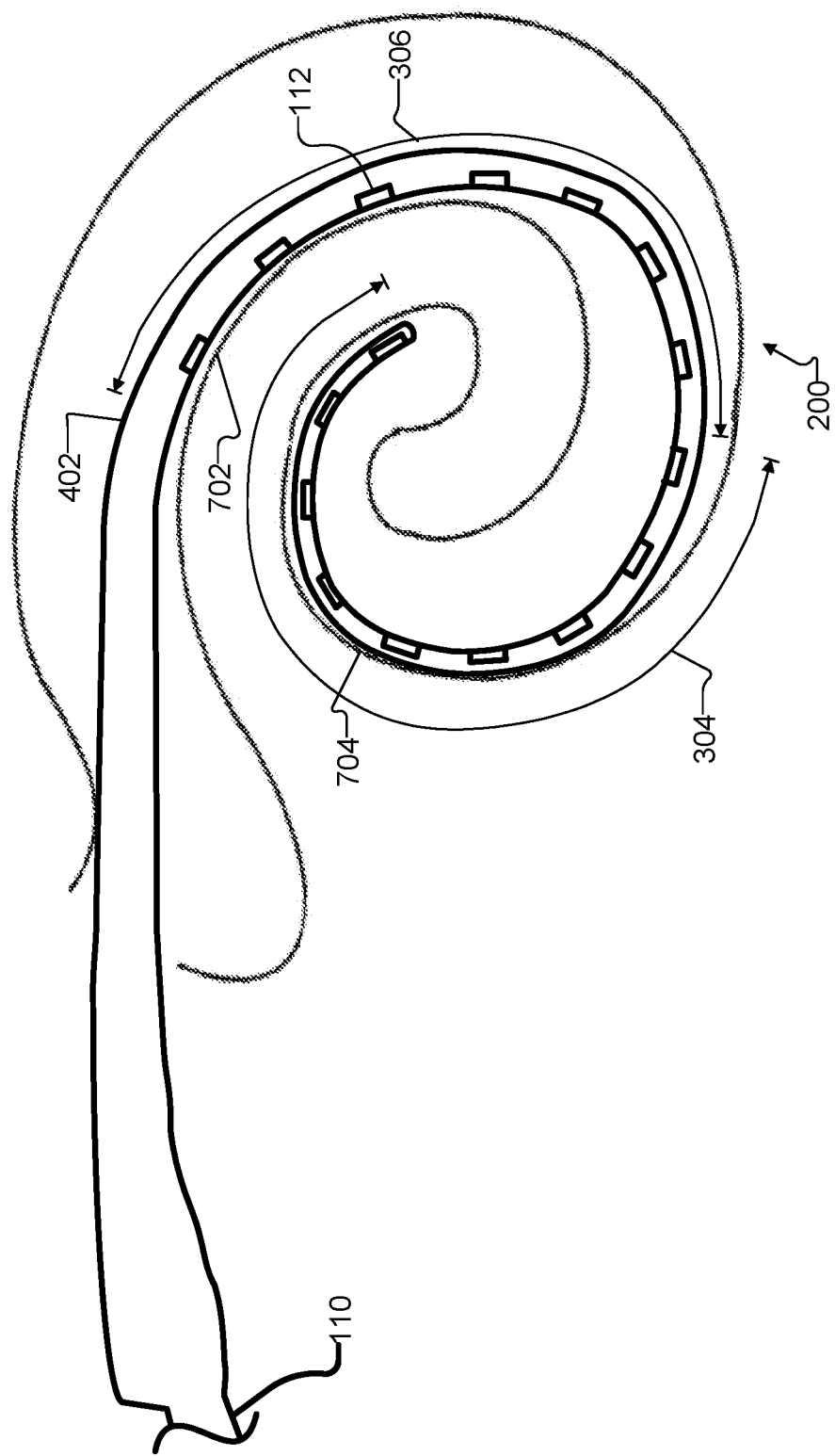
FIG. 7 illustrates an exemplary final insertion position of a peri-straight electrode array according to principles described herein.

FIG. 7 shows an exemplary position of peri-straight electrode array 402 after stylet 404 is removed. As shown in FIG. 7, pre-curved proximal portion 306 is positioned at a cochlear mid basal turn 702 whereas the straight distal portion 304 is positioned along a lateral wall 704 of cochlea 200.

Figure 8:
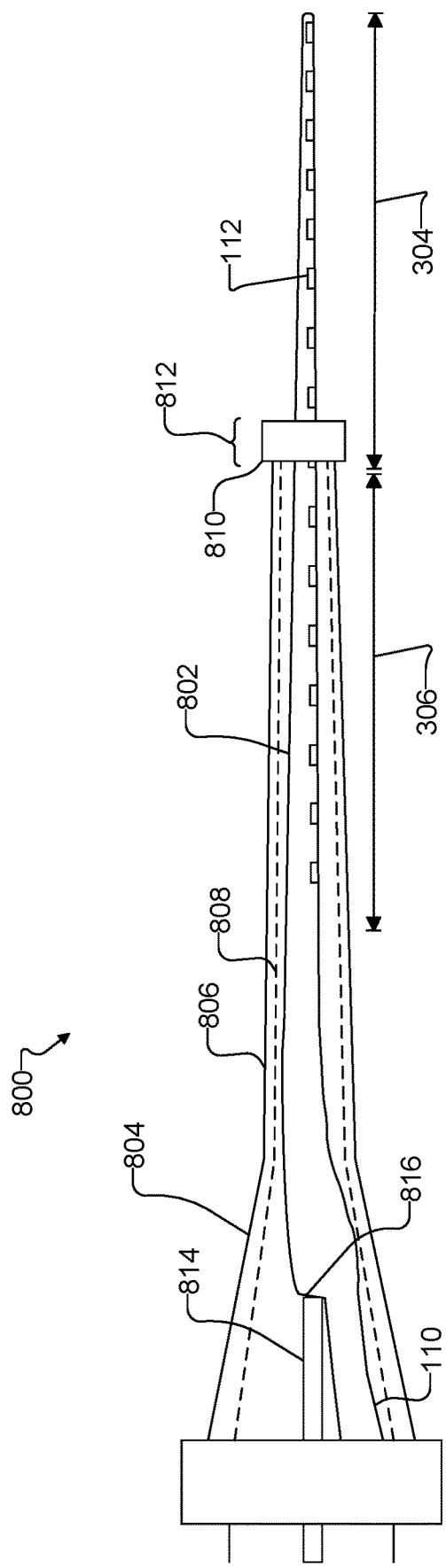
FIG. 8 illustrates a side view of an exemplary assembly including a peri-straight electrode array that has been straightened using a tube according to principles described herein.

FIG. 8 illustrates a side view of an exemplary assembly 800 according to an alternative example in which a peri-straight electrode array 802 is straightened using a tube 804.

As shown, tube 804 has a tube outer diameter 806, a tube inner diameter 808 represented by a dashed line, and a stopper portion 810. Peri-straight electrode array 802 is provided so as to fit within tube inner diameter 808, which causes pre-curved proximal portion 306 to straighten. Although the portions (e.g., pre-curved proximal portion 306) of peri-straight electrode array 802 that overlap with tube 804 are shown in solid lines in FIG. 8, it is understood that those overlapping portions are provided inside of tube 804. Tube 804 may be formed of any suitable material that is sufficiently rigid to cause pre-curved proximal portion 306 to straighten when peri-straight electrode array 802 is inserted within tube 804. In certain examples, tube 804 may be formed of a transparent material such that portions of peri-straight electrode array 802 are visible through tube 804, as shown in FIG. 8. Alternatively, tube 804 may be formed of an opaque material.

As shown in FIG. 8, stopper portion 810 is positioned on a distal end of tube 804. Stopper portion 810 has a relatively larger diameter than other portions (e.g., a portion of tube 804 to the left of stopper portion 810) of the distal end of tube 804. In certain examples, stopper portion 810 may have a diameter that is large enough to prevent tube 804 from entering an insertion opening (e.g., the cochleostomy or the round window) of cochlea 200. In certain alternative examples, stopper portion 810 may not be included on tube 804.

In the example shown in FIG. 8, a portion 812 of tube 804 overlaps a portion of straight distal portion 304 such that straight distal portion 304 is substantially straight with respect to a straightened pre-curved proximal portion 306 while peri-straight electrode array 802 is provided within tube 804. Portion 812 of tube 804 may overlap the portion straight distal portion 304 by any suitable amount. Similar to the example shown in FIG. 4, portion 812 of tube 804 may overlap distal straight portion 304 by approximately 1 mm to 4.5 mm.

As shown in FIG. 8, a pusher rod 814 is provided within tube 804 to facilitate advancing peri-straight electrode array 802 off of tube 804 during an insertion procedure. Pusher rod 814 is configured to press against a stepped portion 816 on electrode lead 110 to advance peri-straight electrode array 802 off of tube 804. Once pusher rod 814 reaches the distal end of tube 804, electrode lead 110 and peri-straight electrode array 802 are released from tube 804 (e.g., through a slot (not shown) provided in tube 804).

Figure 9:
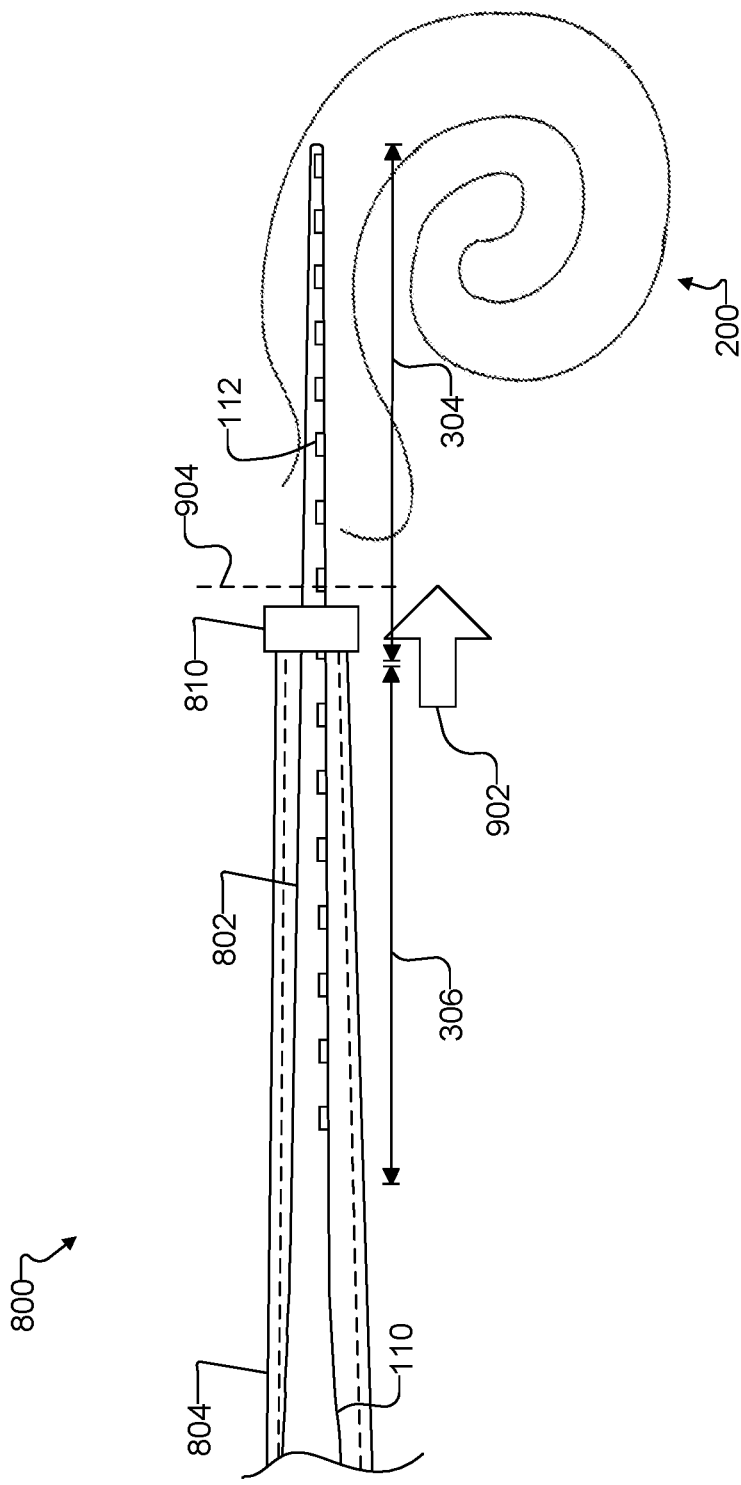
FIGS. 9 and 10 illustrate positions of a peri-straight electrode array during an exemplary insertion procedure that utilizes the assembly illustrated in FIG. 8 according to principles described herein.

FIG. 9 shows a position of a peri-straight electrode array during an exemplary insertion procedure in which assembly 800 is used to insert peri-straight electrode array 802 within cochlea 200. As shown in FIG. 9, tube 804 and peri-straight electrode array 802 are advanced in the direction of arrow 902 until a distal end of tube 804 indicated by stopper portion 810 reaches a position indicated by dashed line 904, which corresponds to a location that is outside of and not touching cochlea 200 of the recipient. When stopper portion 810 reaches the position indicated by dashed line 904, straight distal portion 304 of peri-straight electrode array 802 extends away from the distal end of stopper portion 810 and into cochlea 200.

Once stopper portion 810 is at the position indicated by dashed line 904, the operator of assembly 800 manually interacts with tube 804 by advancing pusher rod 814 in the direction indicated by arrow 902 such that straight distal portion 304 and at least some of pre-curved proximal portion 306 enter into cochlea 200. This is done without allowing tube 804 to enter or come in contact with cochlea 200 during the entirety of the insertion procedure, thereby avoiding potentially damaging cochlea 200 and/or causing the surgeon to lose visibility and/or tactile feedback.

Figure 10:
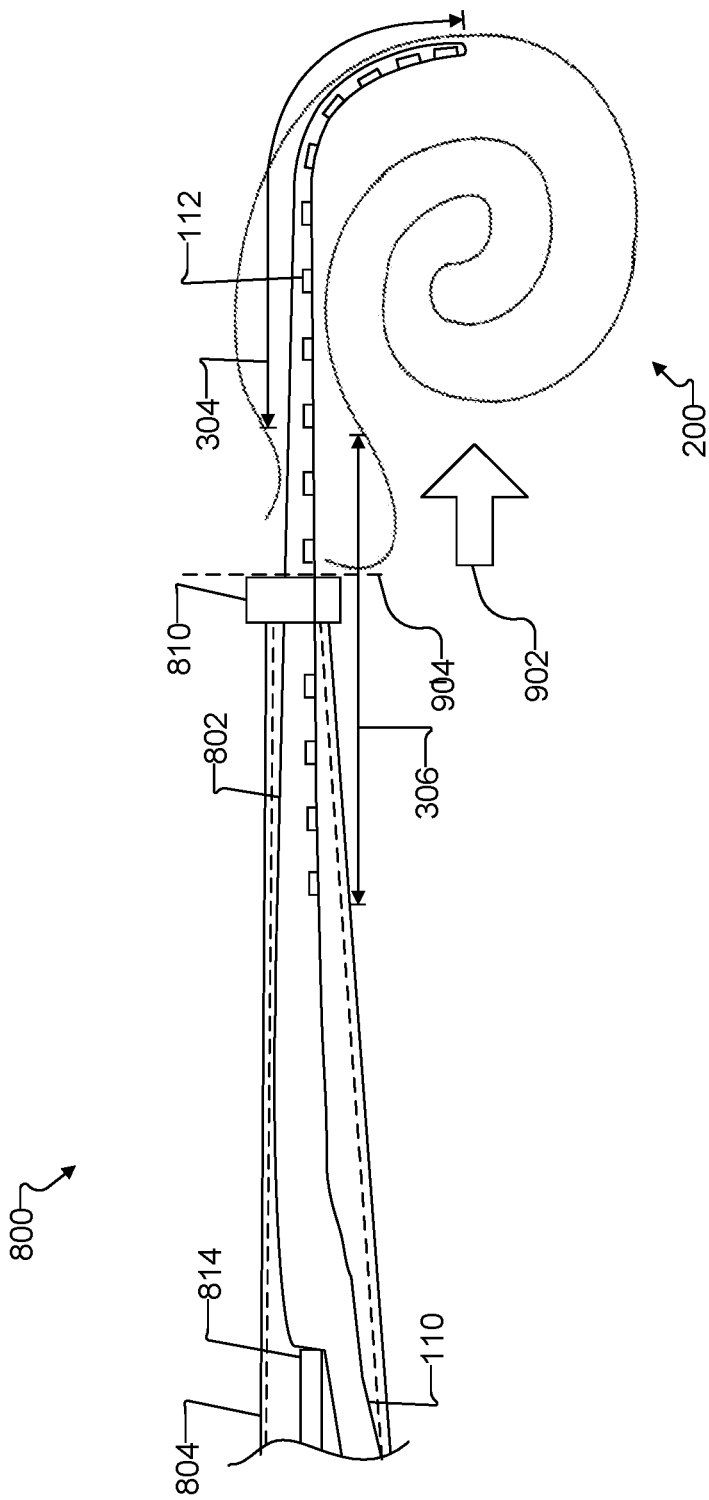

FIG. 10 is an illustration showing peri-straight electrode array 802 in the process of being advanced off of tube 804 and into cochlea 200. As shown in FIG. 10, this is performed without tube 804 advancing beyond the position indicated by dashed line 904. As straight distal portion 304 of peri-straight electrode array 802 enters further within cochlea 200, straight distal portion 304 flexes so as to generally follow a trajectory of a lateral wall of cochlea 200. As peri-straight electrode array 802 is advanced off of tube 804 (e.g., by pusher rod 814 pushing against an stepped portion 816 on electrode lead 110), pre-curved proximal portion 306 returns to its native curved state so as to conform with the helical shape of cochlea 200. In so doing, peri-straight electrode array 802 may achieve a final position similar to that illustrated in FIG. 7.

Figure 11:
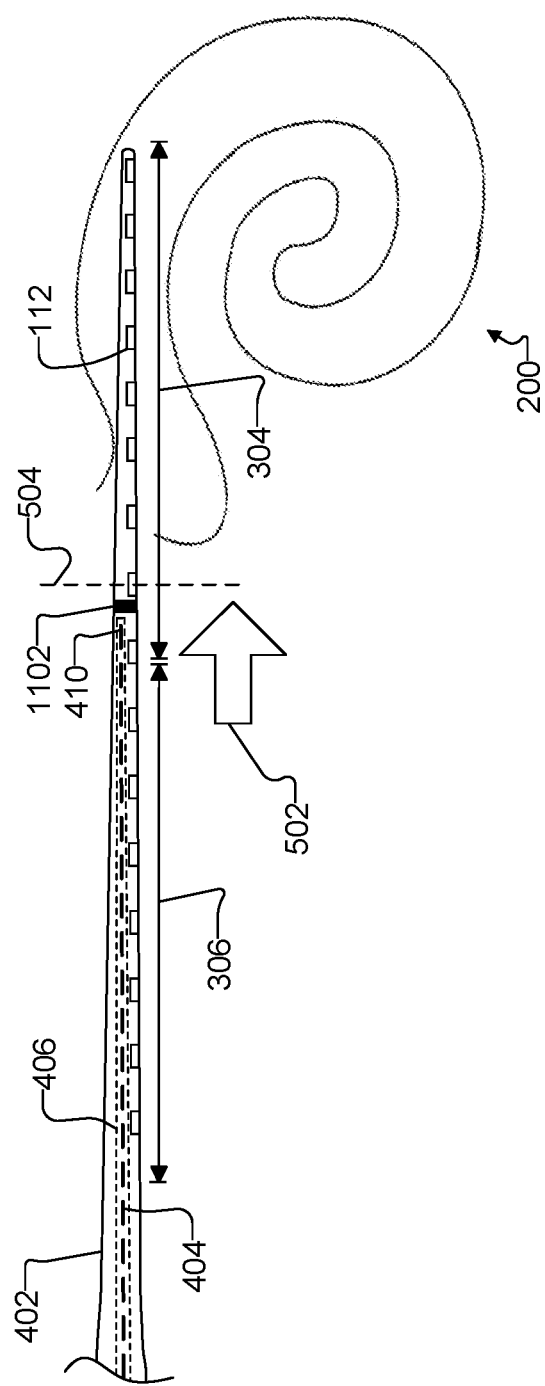
FIGS. 11 and 12 illustrate exemplary assemblies that include one or more indicators to facilitate visualization a peri-straight electrode array during insertion according to principles described herein.

In certain examples, one or more indicators may be provided on an insertion tool and/or a peri-straight electrode array to facilitate visualization of the peri-straight electrode array during insertion and positioning of the peri-straight electrode array and insertion tool within a recipient. Such indicators may be provided in any suitable manner and have any suitable shape, color, and/or size as may serve a particular implementation. For example, an indicator may be provided as a ring that extends around an external surface of a peri-straight electrode array so that a surgeon can visually recognize where an insertion tool is located with respect to cochlea 200 during an insertion procedure. To illustrate, FIG. 11 shows an example in which a peri-straight electrode array 402 includes an indicator 1102 provided as a ring on straight distal portion 304 so as to mark a position of lumen 406. As shown in FIG. 11, a proximal edge of indicator 1102 indicates a distal end of lumen 406 and stylet 404 when stylet 404 is fully engaged within peri-straight electrode array 402. Such a configuration gives surgeons a visual cue to facilitate keeping distal end 410 of stylet 404 outside of cochlea 200 while peri-straight electrode array 402 is advanced off of stylet 404 and into cochlea 200. Although indicator 1102 is shown as being black in FIG. 11, it is understood that indicator 1102 could be of a different color (e.g., blue) in certain implementations.

Figure 12:
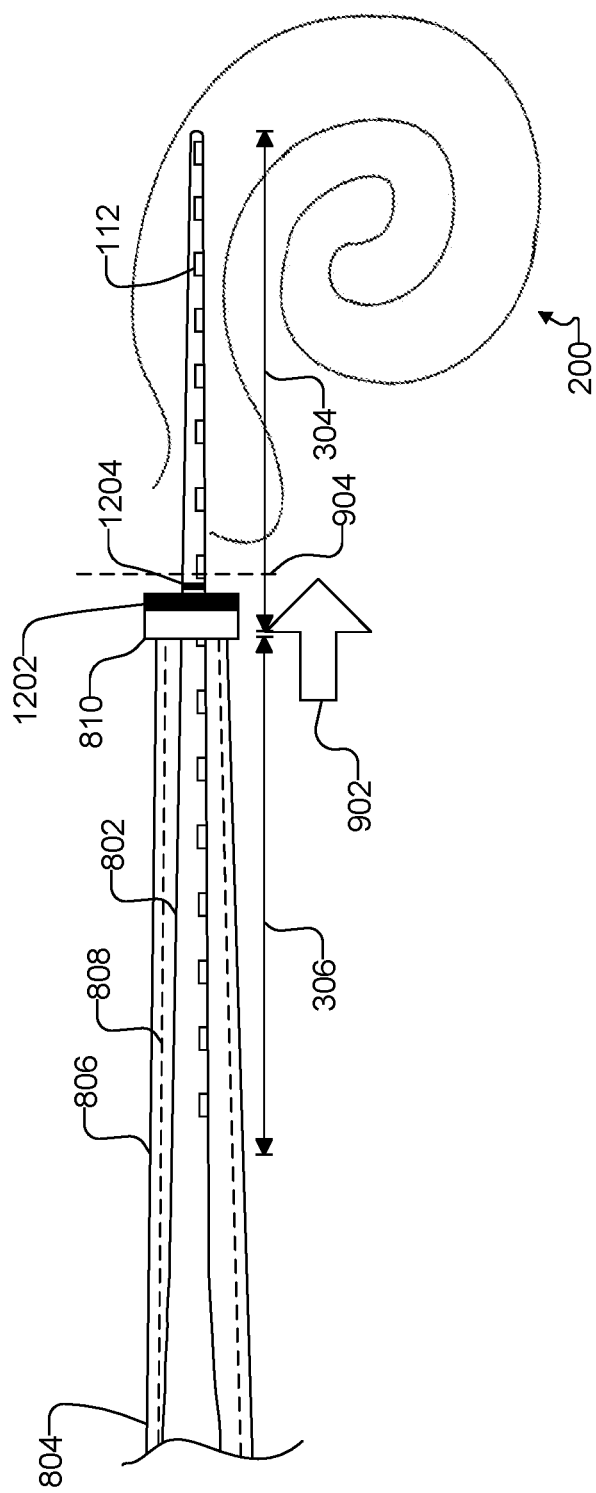

In certain alternative examples, a first indicator may be provided on a distal end of an insertion tool and a second indicator may be provided on the straight distal portion of the peri-straight electrode array. To illustrate, FIG. 12 shows an example in which an indicator 1202 is provided on stopper portion 810 and an indicator 1204 is provided on peri-straight electrode array 802. Indicator 1202 indicates a distal most position of tube 804. As such, a surgeon can easily visualize an insertion depth of peri-straight electrode array 802 and determine when to stop advancing tube 804 such that stopper portion of tube 804 does not touch or enter into cochlea 200.

Indicator 1204 is also configured to facilitate visualization of peri-straight electrode array 802 during insertion. In addition, indicator 1204 may facilitate correctly positioning or repositioning tube 804 over peri-straight electrode array 802 prior to insertion within the recipient. For example, if a surgeon has to reposition peri-straight electrode array 802 within tube 804, the surgeon can line up indicators 1202 and 1204 to ensure that a sufficient amount of straight distal portion 304 extends distally beyond stopper portion 810 prior to insertion. Although indicators 1202 and 1204 are shown as being black in FIG. 12, it is understood that indicators 1202 and 1204 could be colored (e.g., blue) and could have the same or different colors in certain implementations.

Figure 13:
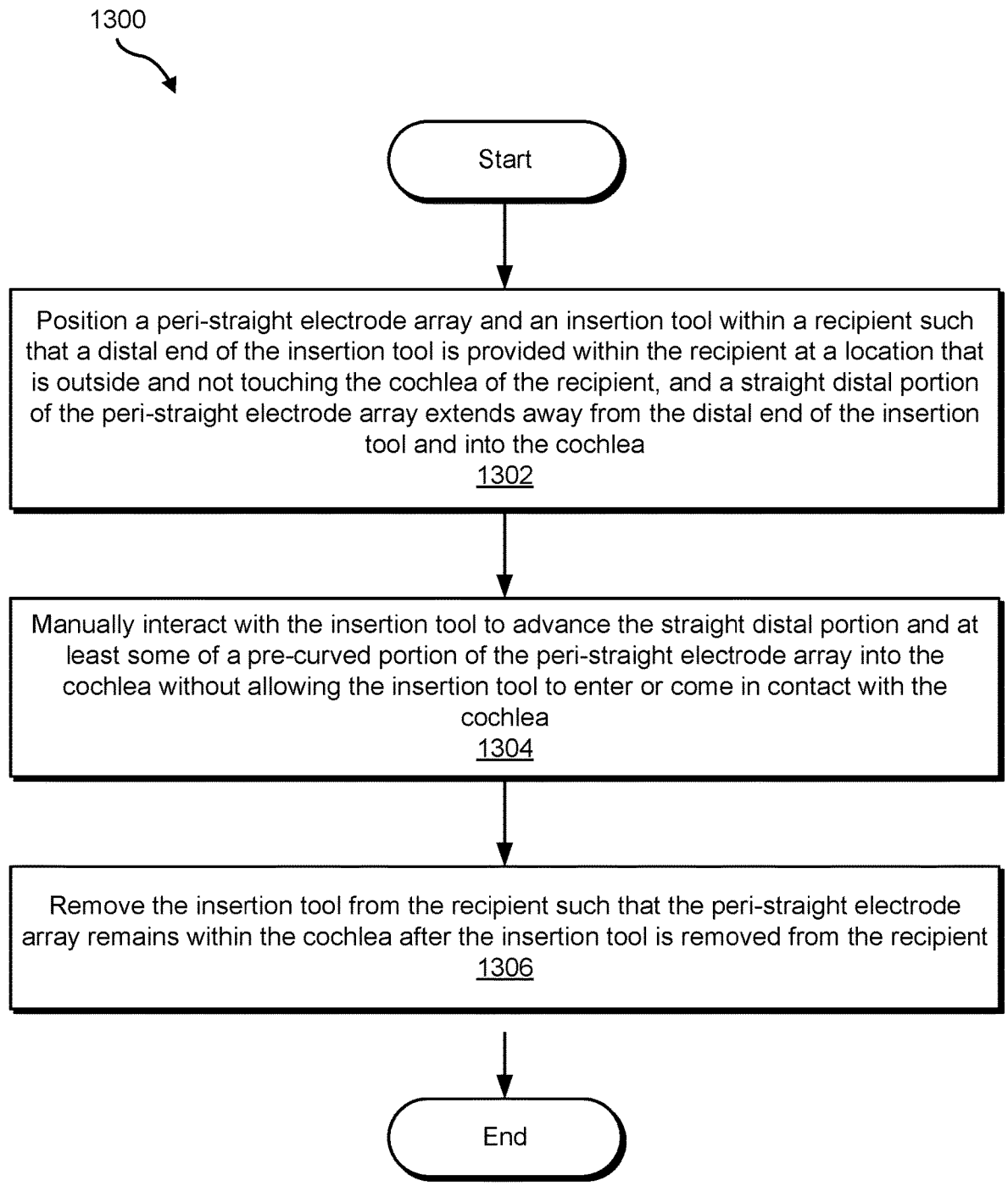
FIGS. 13 and 14 show exemplary methods for inserting a peri-straight electrode array into a cochlea of a recipient according to principles described herein.

FIG. 13 illustrates a method 1300 for inserting a peri-straight electrode array (e.g., peri-straight electrode array 302) into a cochlea of a recipient. While FIG. 13 illustrates exemplary operations according to one embodiment, other embodiments may omit, add to, reorder, and/or modify any of the operations shown in FIG. 13.

In operation 1302, a peri-straight electrode array and an insertion tool are positioned within a recipient such that a distal end of the insertion tool is provided within the recipient at a location that is outside and not touching the cochlea of the recipient, and a straight distal portion of the peri-straight electrode array extends away from the distal end of the insertion tool and into the cochlea. Operation 1302 may be performed in any of the ways described herein.

In operation 1304, an operator (e.g., a surgeon) manually interacts with the insertion tool to advance the straight distal portion and at least some of a pre-curved proximal portion into the cochlea without allowing the insertion tool to enter or come in contact with the cochlea. Operation 1304 may be performed in any of the ways described herein.

In operation 1306, the insertion tool is removed from the recipient such that the peri-straight electrode array remains within the cochlea after the insertion tool is removed from the recipient. Operation 1306 may be performed in any of the ways described herein.

Figure 14:
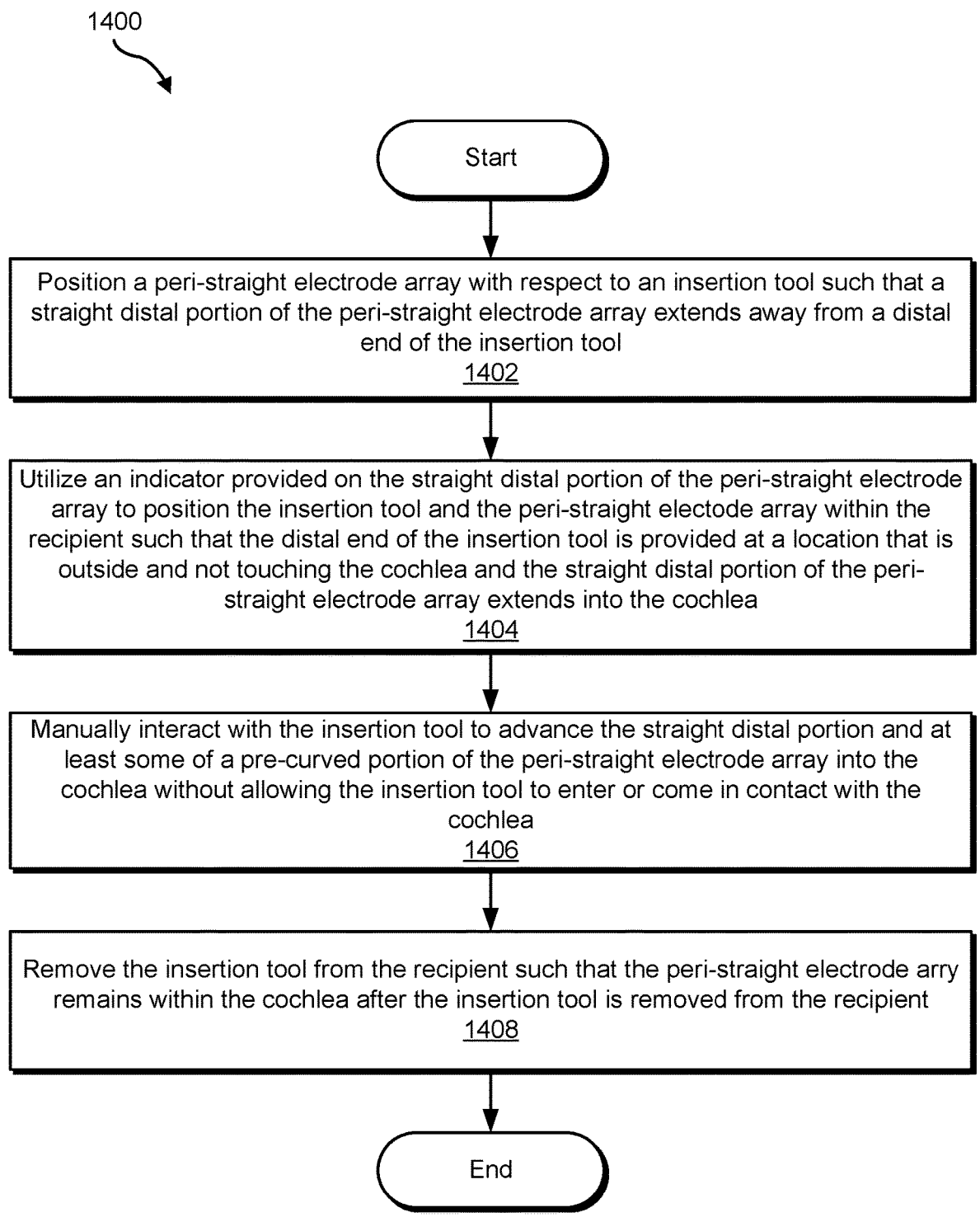

In certain alternative examples, a method for inserting a peri-straight electrode array (e.g., peri-straight electrode array 302) into the cochlea of a recipient may include utilizing an indicator that facilitates visualization of the peri-straight electrode array during insertion. FIG. 14 illustrates a method 1400 for inserting a peri-straight electrode array into the cochlea of a recipient according to such alternative examples. While FIG. 14 illustrates exemplary operations according to one embodiment, other embodiments may omit, add to, reorder, and/or modify any of the operations shown in FIG. 14.

In operation 1402, a peri-straight electrode array is positioned with respect to an insertion tool such that the straight distal portion of the peri-straight electrode array extends away from a distal end of the insertion tool. Operation 1402 may be performed in any of the ways described herein.

In operation 1404, an indicator provided on the straight distal portion of the peri-straight electrode array is utilized to position the insertion tool and the peri-straight electrode array within the recipient such that the distal end of the insertion tool is provided at a location that is outside and not touching the cochlea, and the straight distal portion of the peri-straight electrode array extends into the cochlea. Operation 1404 may be performed in any of the ways described herein.

In operation 1406, an operator (e.g., a surgeon) manually interacts with the insertion tool to advance the straight distal portion and at least some of the pre-curved proximal portion into the cochlea without allowing the insertion tool to enter or come in contact with the cochlea. Operation 1406 may be performed in any of the ways described herein.

In operation 1408, the insertion tool is removed from the recipient such that the peri-straight electrode array remains within the cochlea after the insertion tool is removed from the recipient. Operation 1408 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method of inserting a peri-straight electrode array into a cochlea of a recipient, the peri-straight electrode array including a straight distal portion having a native straight state and a pre-curved proximal portion having a native curved state, the method comprising:
   positioning the peri-straight electrode array and an insertion tool within the recipient such that
      a distal end of the insertion tool is provided within the recipient at a location that is outside and not touching the cochlea of the recipient, and
      the straight distal portion of the peri-straight electrode array extends away from the distal end of the insertion tool and into the cochlea;
   manually interacting with the insertion tool to advance the straight distal portion and at least some of the pre-curved proximal portion into the cochlea without allowing the insertion tool to enter or come in contact with the cochlea; and
   removing the insertion tool from the recipient such that the peri-straight electrode array remains within the cochlea after the insertion tool is removed from the recipient.

2. The method of claim 1, further comprising loading the peri-straight electrode array onto the insertion tool prior to positioning the peri-straight electrode array and the insertion tool within the recipient such that the straight distal portion extends away from the insertion tool prior to being inserted into the recipient.

3. The method of claim 2, wherein the loading of the peri-straight electrode array onto the insertion tool includes overlapping the distal end of the insertion tool with at least a portion of the straight distal portion of the peri-straight electrode array.

4. The method of claim 1, wherein an indicator is provided on the straight distal portion of the peri-straight electrode array, the indicator configured to facilitate visualization of the peri-straight electrode array during insertion and positioning of the peri-straight electrode array and the insertion tool within the recipient.

5. The method of claim 1, wherein:
   the peri-straight electrode array includes a lumen; and
   the insertion tool is a stylet that is provided within the lumen of the peri-straight electrode array so as to straighten the pre-curved proximal portion of the peri-straight electrode array prior to the positioning the peri-straight electrode array and the insertion tool within the recipient.

6. The method of claim 5, wherein:
   a proximal end of the stylet has a first diameter;
   a distal end of the stylet has a second diameter; and
   the second diameter is smaller than the first diameter.

7. The method of claim 5, wherein an indicator is provided on the straight distal portion of the peri-straight electrode array, the indicator indicating a position of a distal end of the lumen and configured to facilitate visualization of the peri-straight electrode array during insertion and positioning of the peri-straight electrode array and the insertion tool within the recipient.

8. The method of claim 1, wherein the insertion tool comprises a tube into which the peri-straight electrode array is inserted so as to straighten the pre-curved proximal portion of the peri-straight electrode array.

9. The method of claim 1, wherein 40% to 60% of the peri-straight electrode array extends distally beyond the distal end the insertion tool prior to the positioning of the peri-straight electrode array and the insertion tool within the recipient.

10. A method of inserting a peri-straight electrode array into a cochlea of a recipient, the peri-straight electrode array including a straight distal portion having a native straight state and a pre-curved proximal portion having a native curved state, the method comprising:
positioning the peri-straight electrode array with respect to an insertion tool such that the straight distal portion of the peri-straight electrode array extends away from a distal end of the insertion tool;
utilizing an indicator provided on the straight distal portion of the peri-straight electrode array to position the insertion tool and the peri-straight electrode array within the recipient such that
the distal end of the insertion tool is provided at a location that is outside and not touching the cochlea, and
the straight distal portion of the peri-straight electrode array extends into the cochlea;
manually interacting with the insertion tool to advance the straight distal portion and at least some of the pre-curved proximal portion into the cochlea without allowing the insertion tool to enter or come in contact with the cochlea; and
removing the insertion tool from the recipient such that the peri-straight electrode array remains within the cochlea after the insertion tool is removed from the recipient.

11. A system comprising:
a peri-straight electrode array configured to be inserted within a cochlea of a recipient, the peri-straight electrode array including a straight distal portion having a native straight state and a pre-curved proximal portion having a native curved state; and
an insertion tool onto which the peri-straight electrode array is configured to be loaded such that the straight distal portion of the peri-straight electrode array extends beyond a distal end of the insertion tool,
wherein 40% to 60% of the peri-straight electrode array extends distally beyond the distal end of the insertion tool to facilitate positioning the peri-straight electrode array within the cochlea of the recipient without the insertion tool entering into or coming in contact with the cochlea during insertion of the peri-straight electrode array into the cochlea.

12. The system of claim 11, wherein the peri-straight electrode array and the insertion tool are provided within a kit in which the insertion tool is pre-loaded onto the peri-straight electrode array.

13. The system of claim 11, wherein:
the peri-straight electrode array includes a lumen; and
the insertion tool is a stylet that is provided within the lumen of the peri-straight electrode array so as to straighten the pre-curved proximal portion of the peri-straight electrode array.

14. The system of claim 13, wherein the stylet overlaps a portion of the straight distal portion of the peri-straight electrode array when the stylet is inserted within the lumen.

15. The system of claim 13, wherein:
a proximal end of the stylet has a first diameter;
a distal end of the stylet has a second diameter; and
the second diameter is smaller than the first diameter.

16. The system of claim 13, wherein the peri-straight electrode array includes an indicator that indicates position of a distal end of the lumen and that provides a visual cue to facilitate positioning peri-straight electrode array within the recipient without the stylet entering the cochlea of the recipient.

17. The system of claim 11, wherein the insertion tool comprises a tube into which the peri-straight electrode array is inserted so as to straighten the pre-curved proximal portion of the peri-straight electrode array.

18. The system of claim 17, wherein the tube overlaps a portion of the straight distal portion of the peri-straight electrode array when the peri-straight electrode array is provided within the tube.

19. The system of claim 17, wherein:
a first indicator is provided on a distal end of the tube;
a second indicator is provided on the straight distal portion of the peri-straight electrode array; and
the first indicator and the second indicator facilitate positioning the peri-straight electrode array with respect to the insertion tool and positioning the peri-straight electrode array within the recipient without allowing the insertion tool to enter into or come in contact with the cochlea during insertion.

20. The system of claim 17, wherein:
a distal end of the insertion tool includes a stopper portion that has a relatively larger diameter than another portion of the distal end of the insertion tool; and
the stopper portion of the insertion tool is configured to prevent the insertion tool from entering the cochlea of the recipient.

* * * * *